United States Patent
Thompson et al.

(10) Patent No.: US 10,918,894 B2
(45) Date of Patent: Feb. 16, 2021

(54) FACE SEAL FOR RESPIRATOR MASK

(71) Applicant: Scott Technologies, Inc., Monroe, NC (US)

(72) Inventors: Darin Kyle Thompson, Huntersville, NC (US); Amy Elizabeth Quiring, Matthews, NC (US); Edward Powers Simmonds, Indian Trail, NC (US); Graham Peter Wilson, Flint (GB); Carl Escort Tucker, Old Colwyn (GB); Christopher Ward, Prestatyn (GB); Kyle Dane Hudson, Denbigh (GB)

(73) Assignee: Scott Technologies, Inc., Monroe, NC (US)

( * ) Notice: Subject to any disclaimer, the term of this patent is extended or adjusted under 35 U.S.C. 154(b) by 213 days.

(21) Appl. No.: 15/769,821

(22) PCT Filed: Oct. 20, 2016

(86) PCT No.: PCT/US2016/057920
§ 371 (c)(1),
(2) Date: Apr. 20, 2018

(87) PCT Pub. No.: WO2017/070351
PCT Pub. Date: Apr. 27, 2017

(65) Prior Publication Data
US 2019/0151687 A1    May 23, 2019

Related U.S. Application Data

(60) Provisional application No. 62/244,906, filed on Oct. 22, 2015.

(51) Int. Cl.
*A62B 18/08* (2006.01)
*A62B 18/02* (2006.01)
*A61M 16/06* (2006.01)

(52) U.S. Cl.
CPC ......... *A62B 18/08* (2013.01); *A61M 16/0616* (2014.02); *A61M 16/0694* (2014.02); *A62B 18/025* (2013.01)

(58) Field of Classification Search
CPC ..... A61M 16/0605–0622; A62B 18/02; A62B 18/025; A62B 18/08
See application file for complete search history.

(56) References Cited

U.S. PATENT DOCUMENTS 2,591,992 A * 4/1952 Aerick ................. A61M 15/00
128/203.27
4,167,185 A * 9/1979 Lewis ............... A61M 16/0616
128/206.24

(Continued)

FOREIGN PATENT DOCUMENTS

WO    WO 2006/110076    10/2006
WO    WO 2009-029363    3/2009

OTHER PUBLICATIONS

Supplementary EP Search Report for EP 16 85 8217 (dated Jun. 6, 2019), 3 pages.

(Continued)

*Primary Examiner* — Valerie L Woodward (57) ABSTRACT

A respiratory mask includes a body configured to cover a nose and a mouth of a user. The body includes a face seal configured to at least partially seal the body to a face of the user. The face seal includes a standard reflex seal that is configured to engage in physical contact with the face to form a first segment of a seal between the body and the face. The face seal also includes a reverse reflex seal that is configured to engage in physical contact with the face to form a second segment of a seal between the body and the face. This configuration allows the mask body to float in place with respect to the face seal and preserves the seal (Continued)

between the mask and the face, even when the user is talking or moving his or her face.

20 Claims, 5 Drawing Sheets

(56) References Cited

U.S. PATENT DOCUMENTS

| | | | | | |
|---|---|---|---|---|---|
| 4,739,755 | A | * | 4/1988 | White | A61M 16/0611 |
| | | | | | 128/206.12 |
| 5,265,595 | A | * | 11/1993 | Rudolph | A61B 5/097 |
| | | | | | 128/204.18 |
| 5,540,223 | A | * | 7/1996 | Starr | A61M 16/06 |
| | | | | | 128/205.25 |
| 2008/0230068 | A1 | | 9/2008 | Rudolph | |
| 2010/0258131 | A1 | * | 10/2010 | Gaffney | A62B 18/08 |
| | | | | | 128/206.24 |
| 2015/0084235 | A1 | * | 3/2015 | Rose | B29C 45/14 |
| | | | | | 264/279 |

OTHER PUBLICATIONS

International Search Report for PCT International Application No. PCT/US2016/057920, dated Jan. 13, 2017, 2pgs.

* cited by examiner

FACE SEAL FOR RESPIRATOR MASK

CROSS REFERENCE TO RELATED APPLICATIONS

This application is a national stage filing under 35 U.S.C. 371 of PCT/US2016/057920, filed Oct. 20, 2016, which claims the benefit of U.S. Provisional Patent Application No. 62/244,906, filed Oct. 22, 2015, the disclosures of which are incorporated by reference in their entirety herein.

TECHNICAL FIELD

The present application relates generally to respirator masks for respiratory protection. Specifically, the present application relates to respirator mask face seal that provides enhanced comfort for the wearer.

BACKGROUND

Respirator masks are used in environments where individuals are exposed to hazardous materials, such as gases, vapors, aerosols (e.g., dusts, mists, and/or biological agents), and/or the like. Respirator masks come in a large variety of types and sizes, ranging from cheaper, disposable masks to higher cost, reusable masks that include replaceable filtration cartridges. Most respirator masks include a face seal that seals against the user's face. For example, face seals may include flexible lips, gaskets, cushions, and/or the like that engage in physical contact with the user's face to create the seal.

However, it may be difficult for many users to achieve a fit with the mask that is both relatively comfortable and provides an adequate seal. Some users may find that wearing the mask is uncomfortable when a seal is created between the face seal of the mask and the user's face. For example, at least some known face seals exert uneven pressure on the user's face such that higher pressure areas (commonly referred to as "hot spots") of the face seal may result in uncomfortable points of contact with the user's face.

SUMMARY

The invention advantageously provides a respirator mask, in particular an oronasal mask, that includes a face seal having a first portion with a standard reflex seal and a second portion with a reverse reflex seal. Each of the first and second portions may define a U shape having an opening, the opening of the first and second portions being directed in different directions. In particular, the opening of U shape of the first portion is directed away the user's face, whereas the opening of the U shape of the second portion is directed toward the user's face. Put another way, when viewed in cross section from the user's perspective, the first portion (standard reflex seal) is at least substantially convex, whereas the second portion (reverse reflex seal) is at least substantially concave. This configuration provides an excellent seal against the user's face, even when the user's jaws and cheeks are moving. This is because the reverse reflex seal in the second portion of the face seal allows the body of the mask to float over the user's face without breaking the seal.

In one embodiment, an oronasal respirator mask includes a body including an upper portion, a lower portion, and a face seal, the face seal having a standard reflex portion in the upper portion and a reverse reflex seal portion in the lower portion.

In one aspect of this embodiment, the standard reflex seal portion has a cross-sectional U shape having a first bottom and a first opening, and the reverse reflex seal portion has a cross-sectional U shape having a second bottom and a second opening, the first opening being directed in a first direction and the second opening being directed in a second direction, the first and second directions being different.

In another aspect of this embodiment, the body further includes an inner surface and an outer surface opposite the inner surface, a direction from the inner surface to the outer surface being a first direction and a direction from the outer surface to the inner surface being a second direction, the standard reflex seal portion having a cross-sectional U shape with an opening that extends in the first direction.

In another aspect of this embodiment, the body further includes an inner surface and an outer surface opposite the inner surface, a direction from the inner surface to the outer surface being a first direction and a direction from the outer surface to the inner surface being a second direction, the reverse reflex seal portion having a cross-sectional U shape with an opening that extends in the second direction.

In another aspect of this embodiment, a direction from the inner surface to the outer surface is a first direction and a direction from the outer surface to the inner surface is a second direction, the standard reflex seal portion including a first wall that extends from the body in the second direction, a second wall that extends toward the body in the first direction, the first wall and the second wall being at least substantially parallel, and a contact surface extending between the first wall and the second wall.

In another aspect of this embodiment, a direction from the inner surface to the outer surface is a first direction and a direction from the outer surface to the inner surface is a second direction, the reverse reflex seal portion including a first wall that extends from the body in the first direction, a second wall that extends from the first wall in a direction different than the first direction and the second direction, and a third wall that extends from the second wall in the second direction, the first wall and the third wall being at least substantially parallel, the third wall including a contact surface.

In another aspect of this embodiment, the standard reflex seal portion extends along a border of the upper portion such that the standard reflex seal portion is configured to engage in physical contact with a user's face adjacent the user's nose when the user is wearing the mask.

In another aspect of this embodiment, the reverse reflex seal portion extends along a border of the lower portion such that the reverse reflex seal portion is configured to engage in physical contact with a user's face adjacent the user's mouth when the user is wearing the mask.

In another aspect of this embodiment, the respiratory mask further includes a frame, the body being overmolded onto the frame, the frame being composed of a first material having a first durometer and the body and face seal being composed of a second material having a second durometer, the first durometer being greater than the second durometer.

In another aspect of this embodiment, the frame and the body together define at least one opening configured to receive an attachable component.

In another aspect of this embodiment, the face seal further has a transition portion between the standard reflex seal portion and the reverse reflex seal portion. In another aspect of this embodiment, the transition portion is at least substantially planar.

In another aspect of this embodiment, the body further includes at least one attachment element configured to engage a harness.

In another embodiment, an oronasal respiratory mask includes a body including an upper portion, a lower portion, and a face seal, the face seal having a convex first seal that extends along a border of the upper portion, the convex first seal having a first cross-sectional U shape defining an opening that is directed in a first direction, and a concave second seal extending along a border of the lower portion, the concave second seal having a second cross-sectional U shape defining an opening that is directed in a second direction, the first direction and the second direction being at least substantially opposite each other.

In another aspect of this embodiment, the first direction is away from a user's face and the second direction is toward the user's face when the user is wearing the mask.

In another aspect of this embodiment, the convex first seal has a first wall extending from the body in the second direction, a second wall extending toward the body in the first direction, the first wall and the second wall being at least substantially parallel, and a sealing land extending between the first wall and the second wall.

In another aspect of this embodiment, the concave second seal has a first wall extending from the body in the first direction, a second wall extending from the first wall in a direction different than the first direction and the second direction, and a third wall extending from the second wall in the second direction, the first wall and the third wall being at least substantially parallel. In another aspect of this embodiment, the third wall of the concave second seal includes a sealing surface, the third wall being configured to engage in physical contact with the user's face at the sealing surface when the user is wearing the mask.

In another aspect of this embodiment, the face seal is integrally formed with a single, unitary construction with the body.

In another embodiment, an oronasal respiratory mask includes a frame composed of a first material having a first durometer, and a body composed of a second material having a second durometer that is less than the first durometer, the body being overmolded onto the frame and including a face seal, the face seal being integrally formed with a single, unitary construction with the body. The face seal has a standard reflex seal portion that has a first wall, a second wall, a first opening defined between the first wall and the second wall, and a first contact surface between the first wall and the second wall oppose the first opening, the first wall and the second wall being at least substantially parallel, the first opening being directed in a first direction and the first contact surface being configured to engage in physical contact with a user's face when the user is wearing the mask. The face seal further has a reverse reflex seal portion that has a third wall, a fourth wall, a second opening defined between the third wall and the fourth wall, and a second contact surface on the fourth wall, the second opening being directed in a second direction, the first direction and the second direction being at least substantially opposite each other, the second contact surface being configured to engage in physical contact with the user's face when the user is wearing the mask.

DETAILED DESCRIPTION

The invention advantageously provides a respirator mask, in particular an oronasal mask, that includes a face seal having a first portion with a standard reflex seal and a second portion with a reverse reflex seal. The first portion of the seal is configured to physically engage and provide a seal with the user's face at least substantially proximate the user's nose and cheeks. In other words, the first portion is in the upper portion of the oronasal mask. The second portion of the seal is configured to physically engage and provide a seal with the user's face at least substantially proximate the user's mouth and chin. Further, each of the first and second portions may define a cross-sectional U shape having an opening, the opening of the first and second portions being directed in different directions. In particular, the opening of U shape of the first portion is directed away the user's face, whereas the opening of the U shape of the second portion is directed toward the user's face. Put another way, when viewed in cross section from the user's perspective, the first portion (standard reflex seal) is at least substantially convex, whereas the second portion (reverse reflex seal) is at least substantially concave. This configuration provides an excellent seal against the user's face, even when the user's jaws and cheeks are moving. This is because the reverse reflex seal in the second portion of the face seal allows the body of the mask to "float" over the user's face without breaking the seal between the user and the mask.

Before describing in detail exemplary embodiments that are in accordance with the disclosure, it is noted that components have been represented where appropriate by convention symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
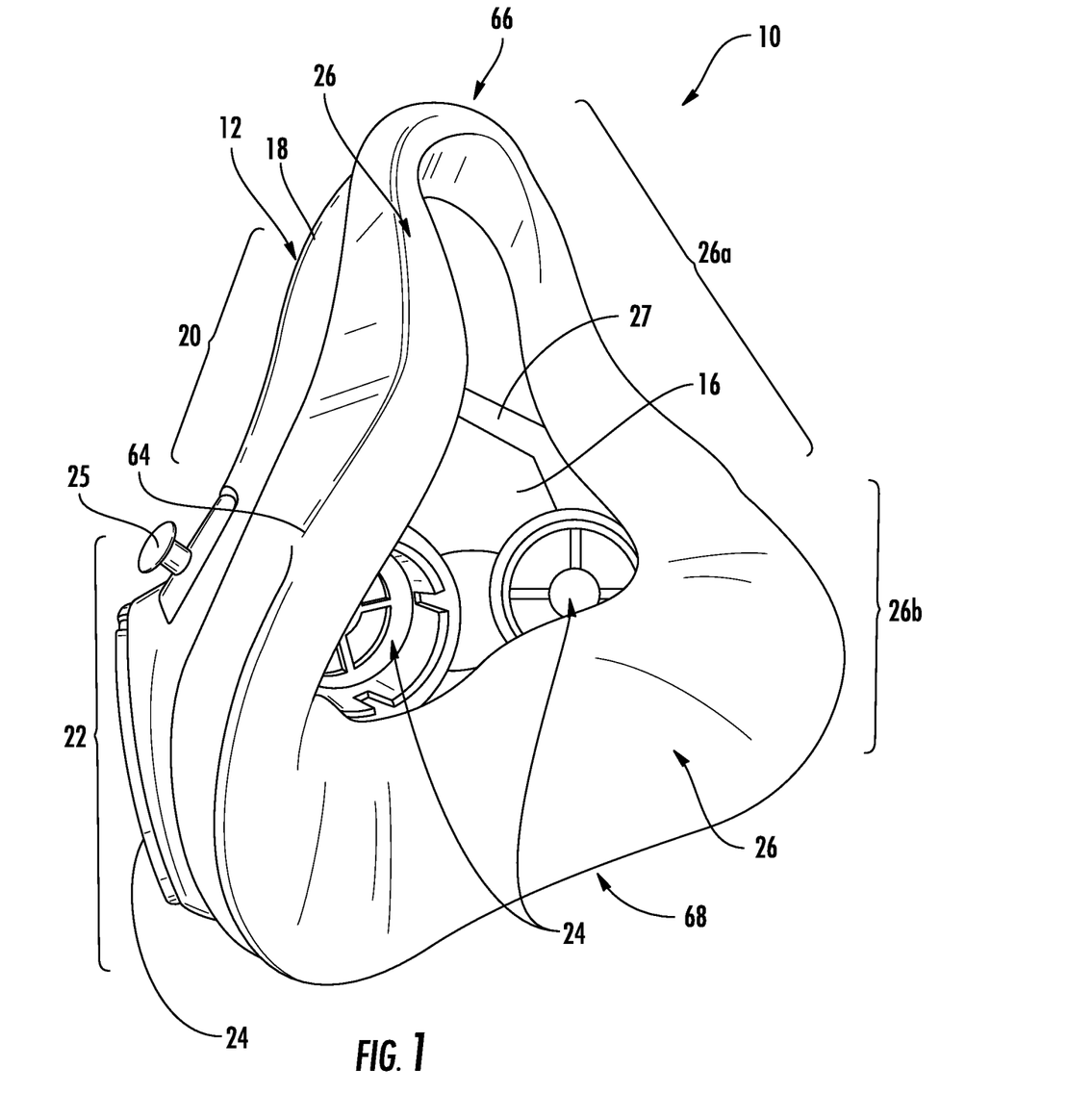
FIG. 1 is a perspective view of an embodiment of a respirator mask for providing respiratory protection.
Figure 4:
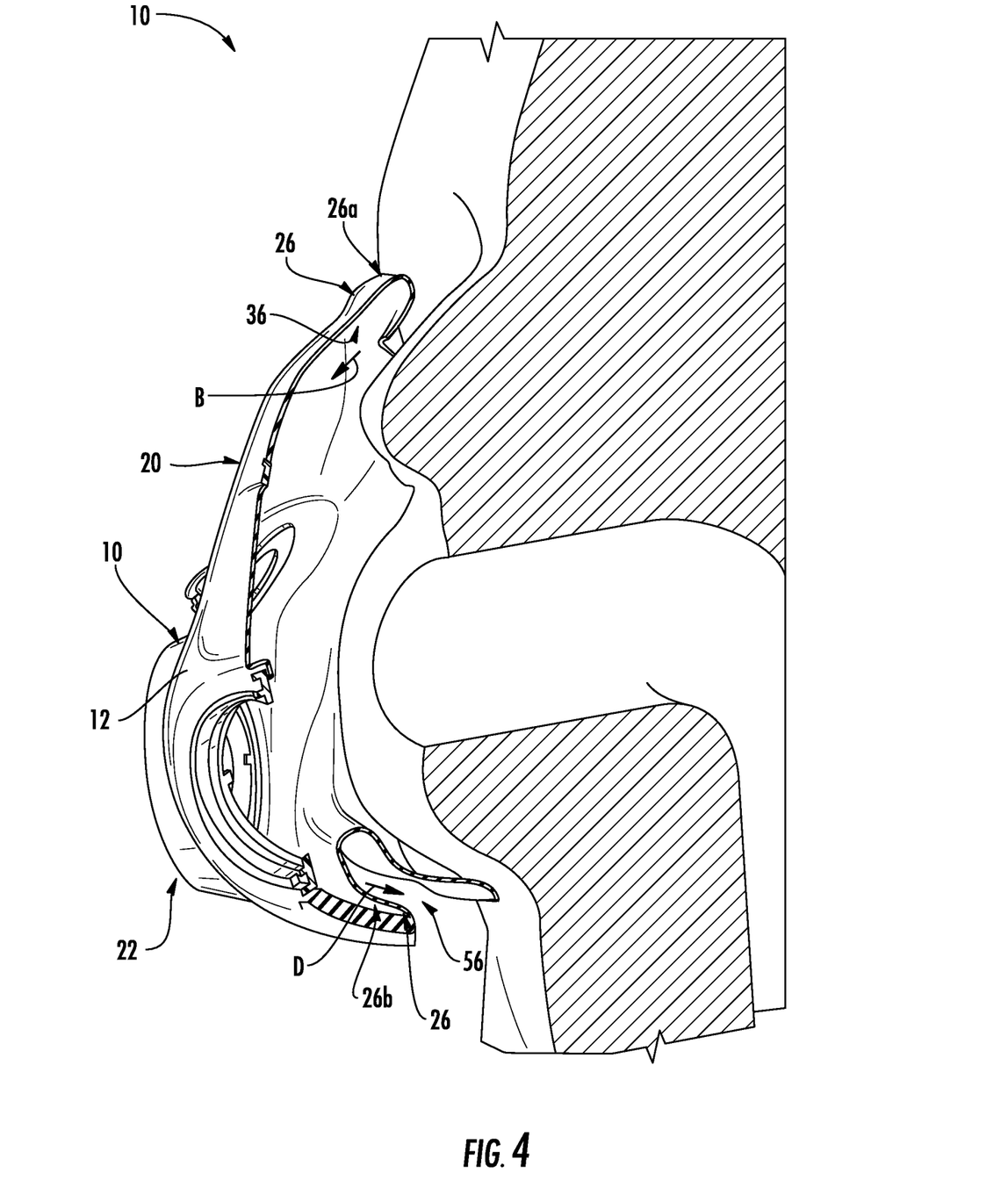
FIG. 4 is a cross-sectional perspective view of the respirator mask shown in FIGS. 1-3 illustrating a cross section of the respirator mask being worn by a user.

Referring now to the drawing figures in which like reference designations refer to like elements, an embodiment of a respirator mask for providing respiratory protection constructed in accordance with the principles of the invention is shown in the figures and generally designated as "10." Referring to FIG. 1, the mask 10 is an oronasal mask configured to be worn by a user in environments where the user is exposed to hazardous materials, such as, but not limited to, gases, vapors, aerosols (such as dusts, mists, and/or biological agents), and/or the like. The mask 10 includes a body 12 that is configured to cover the nose and mouth of the user (for example, as is shown in FIG. 4). As shown herein, the mask 10 is an oronasal half mask that does not cover the user's eyes. However, it will be understood that the mask 10 is not limited to such a configuration, and alternatively may be any other type of mask 10 that is configured to at least partially seal to the user's face.

The body 12 of the mask 10 includes an interior side 16 and an exterior side 18 opposite the interior side 16. The body 12 includes a nose area 20 (which may be referred to as an "upper portion" of the mask body 12) and a mouth area 22 (which may be referred to as a "lower portion" of the mask body 12). The nose area 20 is configured to receive the nose of the user therein such that the nose area 20 covers at least a portion of the user's nose, as is shown in FIG. 4. In the illustrated embodiment, the nose area 20 covers the nose and portions of the upper cheeks of the user. As is also shown in FIG. 4, the mouth area 22 of the mask 10 is configured to cover the user's mouth. In the illustrated embodiment, the mouth area 22 covers the mouth, at least a portion of the chin, and portions of the lower cheeks of the user.

The body 12 of the mask 10 includes one or more openings 24. Each opening 24 is configured to receive one or more attachable components (not shown), such as a replaceable filter cartridge, a valve, an air hose, and/or a speech module. The body 12 may include any number of the openings 24 depending on the particular application of the mask 10 and the number of attachable components that are used.

Although not shown, the mask 10 optionally includes a harness that is configured to hold the mask body 12 on the user's face and thereby hold the mask 10 in position over the user's nose and mouth. In some embodiments, the harness includes a plurality of straps (not shown) that are attached to the mask body 12 and are configured to secure the mask 10 to the user's head. For example, the mask body 12 may include one or more attachment elements 25 to which the harness may be coupled. However, it will be understood that the harness additionally or alternatively may include any other structure. The harness may be reusable. Optionally, the harness is disposable. The harness is optionally fabricated using materials that are relatively easy to sterilize with relatively common sterilization methods.

The mask body 12 may be composed of any suitable material(s). For example, the mask body 12 may be composed of one or more materials that provide the body 12 with at least some flexibility. Examples of suitable materials include, but are not limited to, thermosets, thermoplastics, elastomers, thermoplastic elastomers, cushioning and/or dampening materials, shape memory materials, and/or the like.

The mask body 12 includes a face seal 26 that is configured to at least partially seal the mask against the user's face. As will be described in more detail below, the face seal 26 includes both a standard reflex seal 26a that forms a first segment of the seal and a reverse reflex seal 26b that forms a second segment of the seal. The standard reflex seal 26a and the reverse flex seal 26b are referred to collectively as "seal 26". As shown in FIG. 1, the standard reflex seal 26a extends along the nose area 20 of the mask body 12. The standard reflex seal 26a thus is configured to at least partially seal the nose area 20 of the body 12 with the user's face by engaging in physical contact with the user's face adjacent the user's nose. The reverse reflex seal 26b of the face seal 26 extends along the mouth area 22 of the mask body 12, as is also shown in FIG. 1. Accordingly, the reverse reflex seal 26b is configured to at least partially seal the mouth area 22 of the body 12 with the user's face by engaging in physical contact with the user's face adjacent the user's mouth. The standard reflex seal 26a and the reverse reflex seal 26b may each be referred to herein as a "first seal" and a "second seal," respectively.

Figure 2:
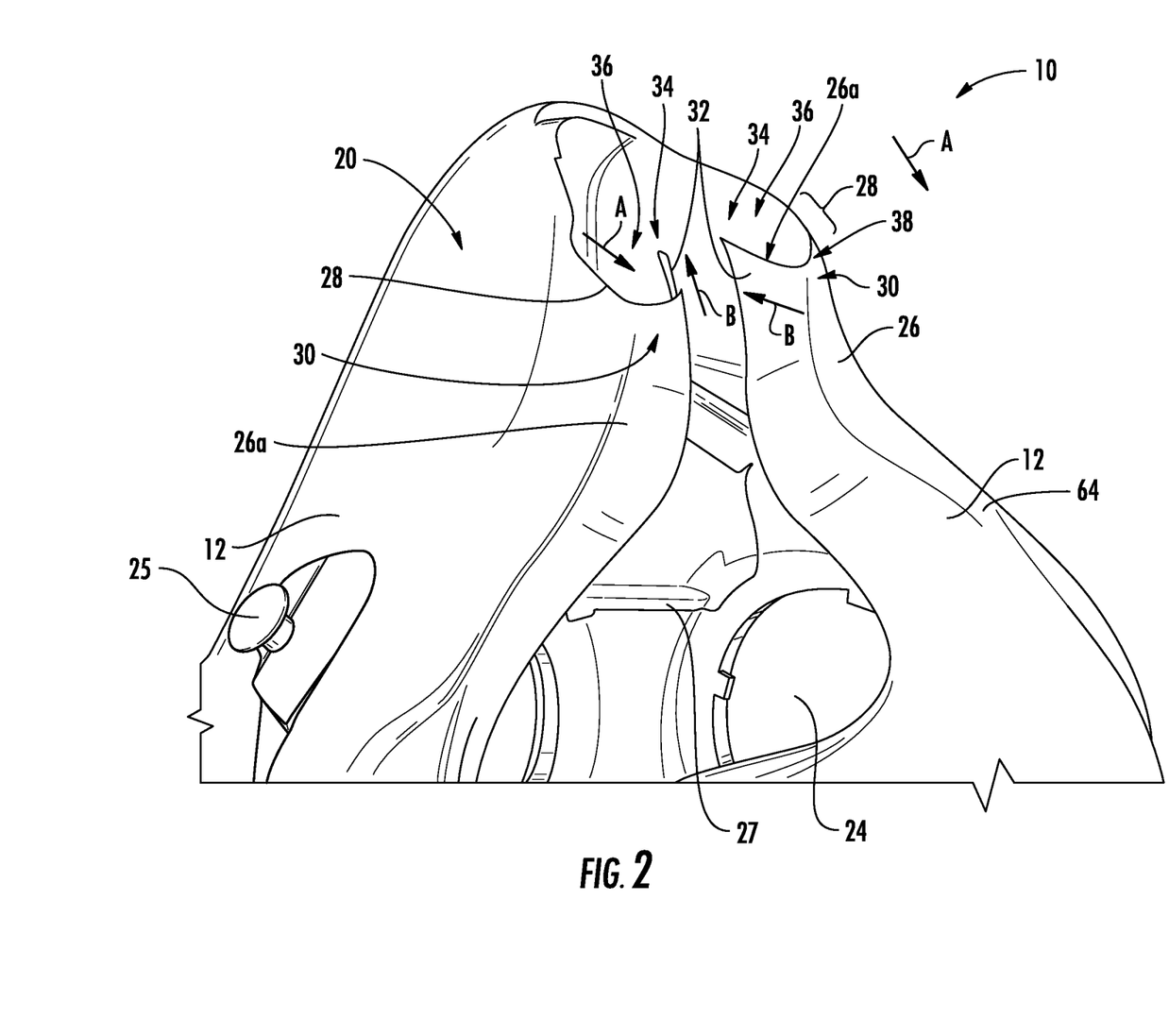
FIG. 2 is a partially cross-sectional perspective view of a portion of the respirator mask shown in FIG. 1.

FIG. 2 is a partially cross-sectional perspective view of a portion of the mask 10 illustrating an embodiment of the standard reflex seal 26a of the face seal 26. A portion of the nose area 20 of the mask body 12 has been cut away from FIG. 2 to illustrate the configuration of the standard reflex seal 26a. The standard reflex seal 26a is defined by a relatively flexible lip that extends along the nose area 20 of the mask body 12. For example, the mask 10 may include a rigid frame 27 over which the body 12 and seal 26 are molded. The entire seal 26, including the standard reflex seal 26a, is composed of a material having a lower durometer than the frame 27. As a non-limiting example, the frame 27 may be composed of a rigid plastic, such as high-density polyethylene (HDPE), whereas the rest of the mask body 12, including the seal 26, may be composed of silicone rubber, thermoplastic elastomer (TPE), or other material that is more flexible than the frame 27.

The standard reflex seal 26a includes a first wall 28 that extends outward from the mask body 12 to a sealing land 30, which may also be referred to as a contact surface, in a direction A (directionality shown with an arrow in the figures). The direction A of the first wall 28 extends generally toward the user's face (i.e., generally away from the mask body 12) when the user is wearing the mask 10. In other words, when the user is wearing the mask 10, the first wall 28 extends outward from the mask body 12 in a direction (i.e., the direction A) generally toward the user's face. FIG. 2 shows two arrows for direction A, which are not shown as being parallel. It will be understood that direction arrows are shown relative to the portion of the mask with which the arrows are associated.

The standard reflex seal 26a includes a second wall 32 that extends outward from the sealing land 30 to a free end 34 of the second wall 32. In other words, the first wall 28 and the second wall 32 intersect each other at the sealing land 30. The second wall 32 extends outward from the sealing land 30 in a direction B, which extends generally away from the user's face (i.e., generally toward the mask body 12) when the user is wearing the mask 10. The first wall 28 and the second wall 32 are at least substantially parallel.

As can be seen in FIG. 2, the relative geometry of the first wall 28, the sealing land 30, and the second wall 32 provides the standard reflex seal 26a with a U shape in cross section (that is, a cross-sectional U shape). The U shape of the standard reflex seal 26a has an opening 36 and a bottom 38 defined by the sealing land 30, opposite the opening 36 that forms the curved portion of the U shape. Put another way, the opening 36 and the bottom 38 each extend between the first wall 28 and the second wall 32 and are on opposite ends of the first wall 28 and the second wall 32 from each other. The bottom 38 also may be referred to as an "apex" and extends between the first wall 27 and the second wall 32. The free end 40 is located within the interior of the mask 10 because of the configuration of the standard reflex seal 26b and directionality of the opening 36. As shown in FIG. 2, the opening 36 of the U shape of the standard reflex seal 26a is in direction B, extending away from the user's face and the bottom 38. In other words, when the user is wearing the mask 10, the opening 36 of the U-shape of the standard reflex seal 26a generally extends away from the user's face.

The sealing land 30 of the standard reflex seal 26a is configured to engage in physical contact with the user's face to form a seal between the standard reflex seal 26a and the user's face. As shown in FIG. 1, the illustrated embodiment of the standard reflex seal 26a is a continuous sealing member along the nose area 20 of the mask body 12.

The illustrated embodiment of the standard reflex seal 26a is integrally formed as a single, unitary structure with the remainder of the body 12. For example, at least the first wall 28 is integrally formed as a single, unitary structure with the remainder of the body 12 in the illustrated embodiment. However, the first wall 28 and/or any other structure of the standard reflex seal 26a may be a discrete component that is attached to the mask body 12. In some embodiments, the structure of the standard reflex seal 26a includes a reusable discrete molded member (for example, the first wall 28) that is attached to the mask body 12. Optionally, the standard reflex seal 26a is defined by a portion of a filtering structure (not shown) of the mask body 12, as is common in many disposable respirator masks wherein the body of the mask is fabricated from a filter material.

The standard reflex seal 26a may be composed of one or more materials that provide one or more of the various structures of the standard reflex seal 26a, such as the wall 28, the sealing land 30, and/or the wall 32, with at least some flexibility. In some embodiments, one or more of the structures of the standard reflex seal 26a are sufficiently flexible such that the standard reflex seal 26a is configured to conform to the size and shape of a range of different faces. For example, the same mask may be used by a number of users, each having different face geometry and feature sizes, because of the flexibility of the seal 26, including the standard reflex seal 26a. Examples of suitable materials include, but are not limited to, thermosets, thermoplastics, elastomers, thermoplastic elastomers, cushioning and/or dampening materials, shape memory materials, and/or the like.

The various design parameters of the various structures of the standard reflex seal 26a, such as, but not limited to, the material(s), the amount of flexibility, the dimensions, the shape, the orientation, the position, the location, and/or the like, may be selected to enable the standard reflex seal 26a to provide a predetermined seal with the user's face.

Figure 3:
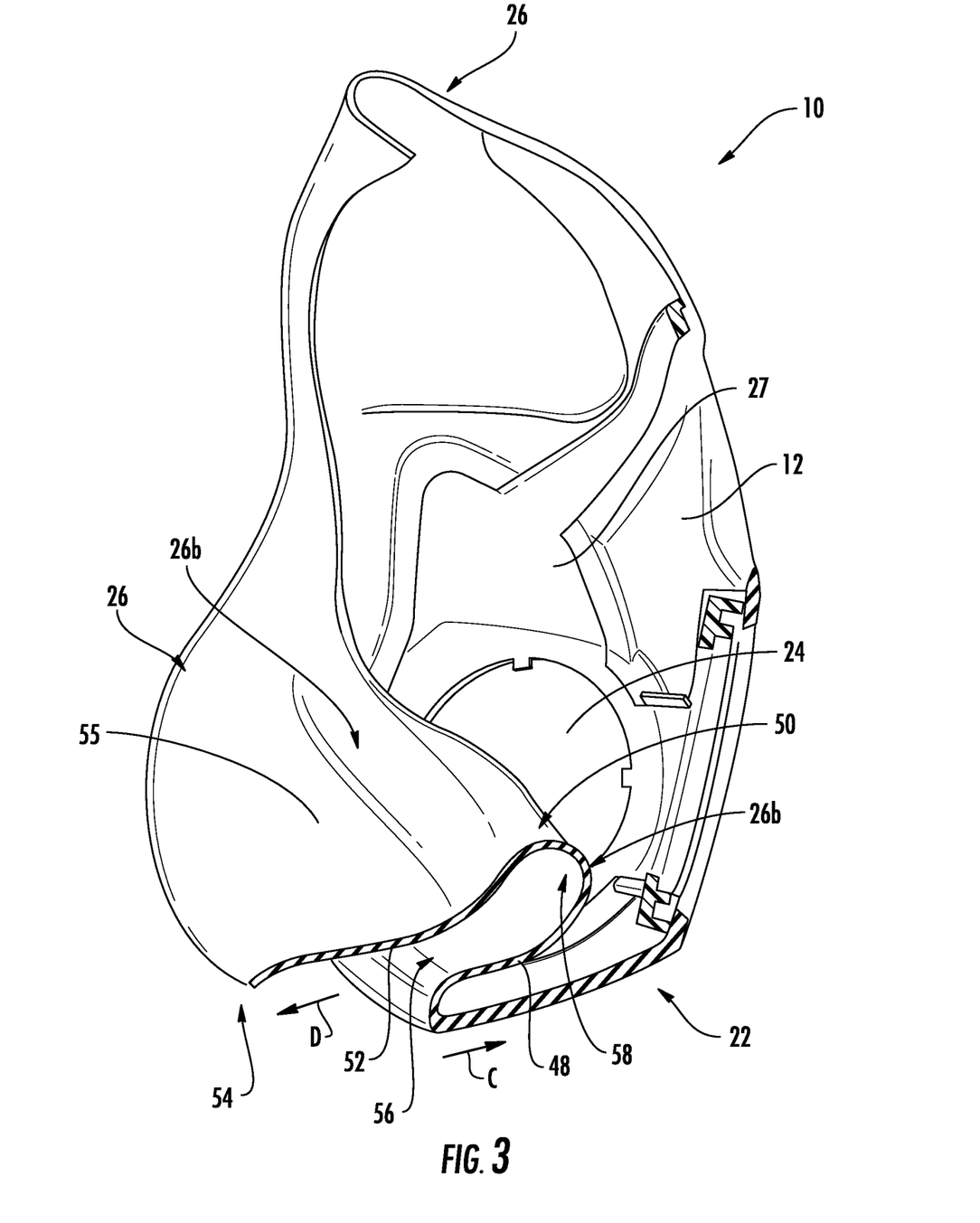
FIG. 3 is a cross-sectional side view of the respirator mask shown in FIGS. 1 and 2.
Figure 5:
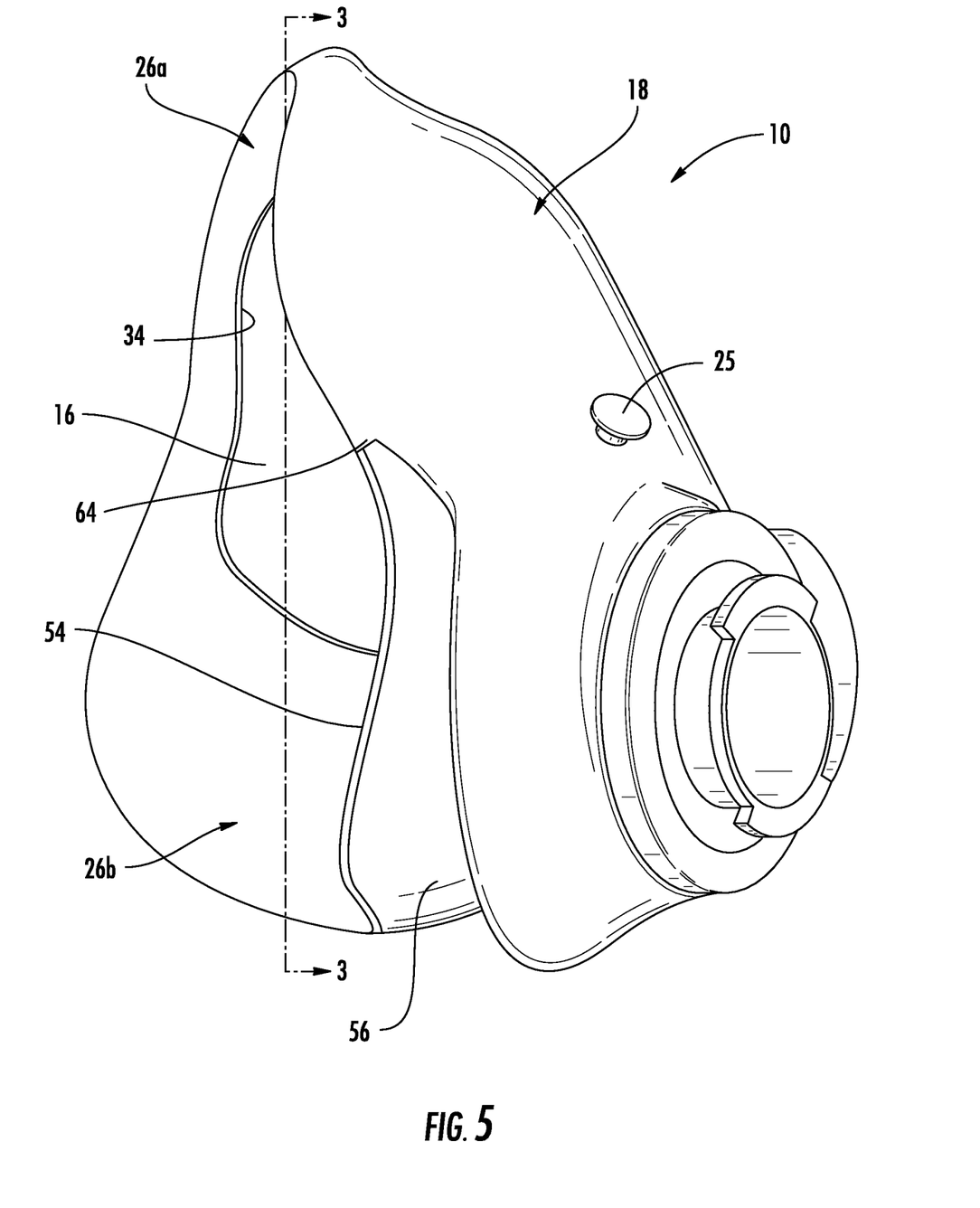
FIG. 5 is a side view of an embodiment of the respirator mask shown in FIG. 1.

FIG. 3 is a cross-sectional side view of the mask 10, with the mask body 12 cut along line 3-3 in FIG. 5. FIG. 3 illustrates an embodiment of the reverse reflex seal 26b of the face seal 26. The reverse reflex seal 26b is defined by a relatively flexible lip that extends along the mouth area 22 of the mask body 12. For example, the entire seal 26, including the reverse flex seal 26b, is composed of a material having a lower durometer than the frame 27. The reverse reflex seal 26b includes a first wall 48 that extends from the mask body 12 in a direction C to a second wall 50. The direction C of the first wall 48 extends generally away from the user's face (that is, generally toward the mask body 12) when the user is wearing the mask 10. In other words, when the user is wearing the mask 10, the first wall 48 of the reverse reflex seal 26b extends from the mask body 12 in direction C, generally away from the user's face.

The reverse reflex seal 26b includes a third wall 52 that extends outward from the second wall 50 to a free end 54 of the third wall 52. In other words, the first wall 48 and the third wall 52 intersect each other at the second wall 50. The third wall 52 extends outward from the second wall 50 in a direction D, which extends generally toward the user's face (that is, generally away from the mask body 12) when the user is wearing the mask 10. The first wall 48 and the third wall 52 are at least substantially parallel.

The third wall 52 of the reverse reflex seal 26b is configured to engage in physical contact with the user's face to form a seal between the reverse reflex seal 26b and the user's face. Specifically, a sealing surface 55, which may also be referred to as a "contact surface," of the third wall 52 is configured to engage in physical contact with the user's face to form the seal between the reverse reflex seal 26b and the user's face. The sealing surface 55 may also be referred to as a sealing land or a contact surface. The second wall 50 functions like a spring to provide a reactive sealing force for pressing the sealing surface 55 against the user's face. As shown in FIG. 1, the illustrated embodiment of the reverse reflex seal 26b is a continuous sealing member along the mouth area 22 of the mask body 12.

As can be seen in FIG. 3, the relative geometry of the first wall 48, the second wall 50, and the third wall 52 provides the reverse reflex seal 26b with a U shape in cross section. The U shape of the reverse reflex seal 26b has an opening 56 and a bottom 58, defined by the second wall 50, opposite the opening 56 that forms the curved portion of the U shape. The bottom 58 also may be referred to as an "apex." Put another way, the opening 56 and the bottom 58 (and the second wall 50) each extend between the first wall 48 and the third wall 52 and are on opposite ends of the first wall 48 and the third wall 52 from each other. The opening 56 of the U shape of the reverse reflex seal 26b is in the direction D, extending toward the user's face. In other words, when the user is wearing the mask 10, the opening 56 of the U shape of the reverse reflex seal 26b points generally toward the user's face. As best seen in FIG. 4, the openings 36 and 56 of the U shapes of the standard and reverse reflex seals 26a and 26b, respectively, point in different directions from each other. That is, the U shape of the standard reflex seal 26a opens in direction B, away from the user's face, and the U shape of the reverse reflex seal 26b opens in direction D, toward the user's face.

The illustrated embodiment of the reverse reflex seal 26b is integrally formed as a single, unitary structure with the remainder of the body 12. For example, the first wall 48 is integrally formed as a single, unitary structure with the remainder of the body 12 in the illustrated embodiment. However, the first wall 48 and/or any other structure of the reverse reflex seal 26b may be a discrete component that is attached to the mask body 12. In some embodiments, the structure of the reverse reflex seal 26b includes a reusable discrete molded member (for example, the first wall 48) that is attached to the mask body 12. Optionally, the reverse reflex seal 26b is defined by a portion of a filtering structure (not shown) of the mask body 12, as is common in many disposable respirator masks wherein the body of the mask is fabricated from a filter material.

The reverse reflex seal 26*b* may be composed of one or more materials that provide one or more of the various structures of the reverse reflex seal 26*b*, such as the first wall 48, the second wall 50, and/or the third wall 52, with at least some flexibility. In some embodiments, one or more of the structures of the reverse reflex seal 26*b* are sufficiently flexible such that the reverse reflex seal 26*b* is configured to conform to the size and shape of a range of different faces. For example, the same mask may be used by a number of users, each having different face geometry and feature sizes, because of the flexibility of seal, including the reverse reflex seal 26*b*. Examples of suitable materials include, but are not limited to, thermosets, thermoplastics, elastomers, thermoplastic elastomers, cushioning and/or dampening materials, shape memory materials, and/or the like.

The various design parameters of the various structures of the reverse reflex seal 26*b*, such as, but not limited to, the material(s), the amount of flexibility, the dimensions, the shape, the orientation, the position, the location, and/or the like, may be selected to enable the reverse reflex seal 26*b* to provide a predetermined seal with the user's face.

FIG. 4 is a cross-sectional perspective view of the mask 10 illustrating a cross section of the mask 10 being worn by a user (depicted as a stylized human face), with the mask body 12 cut along line 3-3 in FIG. 5. In the illustrated embodiment, the nose area 20 of the mask body 12 covers the user's nose, while the mouth area 22 of the mask body 12 cover's the user's mouth. The face seal 26 of the mask 10 is engaged in physical contact with the user's face to at least partially seal the mask body 12 to the user's face. Specifically, the standard reflex seal 26*a* is engaged in physical contact with the user's face adjacent the user's nose such that the standard reflex seal 26*a* covers the upper cheeks and nose of the user, as is shown in FIG. 4. The illustrated embodiment of the standard reflex seal 26*a* thus seals the nose area 20 of the mask body 12 with the user's face. As also shown in FIG. 4, the reverse reflex seal 26*b* is engaged in physical contact with the user's face adjacent the user's mouth such that the reverse reflex seal 26*b* covers the chin and lower cheeks of the user. The illustrated embodiment of the reverse reflex seal 26*b* thus seals the mouth area 22 of the mask body 12 with the user's face. In the illustrated embodiment, the standard reflex seal 26*a* and the reverse reflex seal 26*b* form a continuous circumferential sealing member along the mask body 12 and therefore around the user's face.

As shown in FIG. 4, the U shape of the standard reflex seal 26*a* opens in the direction B at the opening 36, which is generally away from the user's face, while the U shape of the reverse reflex seal 26*b* opens in the direction D at the opening 56, which is generally toward the user's face. As described above, the openings 36 and 56 of the U shapes of the standard and reverse reflex seals 26*a* and 26*b*, respectively, point in different directions from each other, in directions B and D, respectively. Further, directions B and D are considered to be opposite each other because the standard reflex seal 26*a* and the reverse reflex seal 26*b* have U shapes with openings that point in generally opposite directions, as described above and shown in FIG. 4, although differences in the mask's fit for each user may cause directions B and D to be at least substantially opposite each other, for example, 180°±45°. When the harness of the mask 10 is tightened around the user's head, the standard reflex seal 26*a* and the reverse reflex seal 26*b* enable the mask body 12 to move in different directions relative to the user's face. Specifically, the standard reflex seal 26*a* pushes the mask body 12 away from the user's face when the harness is tightened. The reverse reflex seal 26*b* enables the mask body 12 to move away from the user's face, which may provide relatively continuous evenly distributed pressure along the face seal 26.

FIG. 5 is a side view of the mask 10, which shows the transition portion 64 in the mask body 12 between the standard reflex seal 26*a* and the reverse reflex seal 26*b*. As discussed above, the openings 36 and 56 of the U shapes of the standard and reverse reflex seals 26*a* and 26*b*, respectively, point in different directions. Additionally, the reverse reflex seal 26*b* includes a free end 54 that is directed away from the mask body 12 and exposed to the exterior of the mask, whereas the free end 40 of the standard reflex seal 26*a* is located within the interior of the mask. As viewed from the side, the standard reflex seal 26*a* is convex and the reverse reflex seal 26*b* is concave. Therefore, the seal 26 includes a transition portion 64 between the standard reflex seal 26*a* and the reverse reflex seal 26*b* in which at least a portion of the seal 26 is at least substantially planar and is neither concave nor convex. The mask body 12 includes a first end 66, a second end 68, and a distance extending between the first 66 and second 68 ends. The transition portion 64 may be located approximately halfway between the first 66 and second 68 ends, however it will be understood that the transition portion 64 may be at any location along the length of the mask body 12 that will provide the best seal for a given user's face.

The U shape of the reverse reflex seal 26*b* and the orientation of the opening 56 along direction D isolates the user's cheeks and chin from the mask body 12, which enables the mask 10 to "float" as the user moves. The reverse reflex seal 26*b* thus maintains the user's chin as snuggly engaged (and thus sealed) with the reverse reflex seal 26*b* during movement of the user. In other words, the reverse reflex seal 26*b* enables the user and the mask 10 to move with respect to each other without breaking the seal between the face seal 26 and the user's face. The sealing surface 55 of the reverse reflex seal 26*b* has a larger surface area than the sealing lands of known standard reflex seals, which may spread the sealing force over a larger area, which may increase the comfort of the seal 26*b* and/or may enable the reverse reflex seal 26*b* to better conform to the size and shape of, and thereby at least partially form a seal with, a range of different faces than known standard reflex seals.

The illustrated face seal 26 may be capable of flexing with every move of the user, which may result in a higher fit factor than known respirator masks. The enhanced comfort and fit provided by the face seal 26 may provide a better user experience, even when the mask is worn for several hours at a time. Accordingly, the face seal 26 may increase a user's tolerance for wearing appropriate personal protective equipment (PPE). The reverse reflex seal 26*b* of the face seal 26 may provide continuous and evenly distributed pressure along the user's chin and lower cheeks. The standard reflex seal 26*a* of the face seal may conform to the size and shape of a range of different faces. The geometry of the standard reflex seal 26*a* at the upper portion of the mask body 10 conforms to the face of the user in the cheek and nose area, which have shapes that change direction relatively rapidly, while the geometry of the reverse reflex seal 26 at the lower portion of the mask body 10 provides a large comfort area for the chin of the user, which has a more uniform shape and may not change direction as quickly as the cheek and nose area of the user. Accordingly, the hybrid design of the face seal 26 with the standard reflex seal 26*a* combined with the reverse reflex seal 26*b* may provide an improved comfort and fit as compared to known respirator mask face seals.

The invention advantageously provides a respirator mask 10, in particular an oronasal mask, that includes a face seal 26 having a first portion 26a with a standard reflex seal and a second portion 26b with a reverse reflex seal. Each of the first 26a and second 26b portions may define a U shape having an opening 36, 56, respectively, the opening 36, 56 of the first 26a and second 26b portions being directed in different directions. In particular, the opening 36 of U shape of the first portion 26a is directed away the user's face, whereas the opening 56 of the U shape of the second portion 26b is directed toward the user's face. Put another way, when viewed in cross section from the user's perspective, the first portion (standard reflex seal) 26a is at least substantially convex, whereas the second portion (reverse reflex seal) 26b is at least substantially concave. This configuration provides an excellent seal against the user's face, even when the user's jaws and cheeks are moving. This is because the reverse reflex seal 26b in the second portion of the face seal 26 allows the mask body 12 to float over the user's face without breaking the seal between the face seal 26 and the user's face.

In one embodiment, an oronasal respirator mask 10 includes a body 12 including an upper portion 20, a lower portion 22, and a face seal 26, the face seal 26 having a standard reflex portion (26a) in the upper portion 20 and a reverse reflex seal portion (26b) in the lower portion (22).

In one aspect of this embodiment, the standard reflex seal portion 26a has a cross-sectional U shape having a first bottom 38 and a first opening 36, and the reverse reflex seal portion 26b has a cross-sectional U shape having a second bottom 58 and a second opening 56, the first opening 36 being directed in a first direction and the second opening 56 being directed in a second direction, the first and second directions being different.

In another aspect of this embodiment, the body 12 further includes an inner surface 16 and an outer surface 18 opposite the inner surface 16, a direction from the inner surface 16 to the outer surface 18 being a first direction and a direction from the outer surface 18 to the inner surface 16 being a second direction, the standard reflex seal portion 26a having a cross-sectional U shape with an opening 36 that extends in the first direction.

In another aspect of this embodiment, the body 12 further includes an inner surface 16 and an outer surface 18 opposite the inner surface 16, a direction from the inner surface 16 to the outer surface 18 being a first direction and a direction from the outer surface 18 to the inner surface 16 being a second direction, the reverse reflex seal portion 26b having a cross-sectional U shape with an opening 56 that extends in the second direction.

In another aspect of this embodiment, a direction from the inner surface to the outer surface is a first direction and a direction from the outer surface to the inner surface is a second direction, the standard reflex seal portion 26b including a first wall 28 that extends from the body 12 in the second direction, a second wall 32 that extends toward the body 12 in the first direction, the first wall 28 and the second 32 wall being at least substantially parallel, and a contact surface 30 extending between the first wall 28 and the second wall 32.

In another aspect of this embodiment, a direction from the inner surface to the outer surface is a first direction and a direction from the outer surface to the inner surface is a second direction, the reverse reflex seal portion 26b including a first wall 48 that extends from the body 12 in the first direction, a second wall 50 that extends from the first wall 48 in a direction different than the first direction and the second direction, and a third wall 52 that extends from the second wall 50 in the second direction, the first wall 48 and the third 52 wall being at least substantially parallel, the third wall 52 including a contact surface 55.

In another aspect of this embodiment, the standard reflex seal portion 26a extends along a border of the upper portion 20 such that the standard reflex seal portion 26a is configured to engage in physical contact with a user's face adjacent the user's nose when the user is wearing the mask 10.

In another aspect of this embodiment, the reverse reflex seal portion 26b extends along a border of the lower portion 22 such that the reverse reflex seal portion 26b is configured to engage in physical contact with a user's face adjacent the user's mouth when the user is wearing the mask 10.

In another aspect of this embodiment, the respiratory mask 10 further includes a frame 27, the body 12 being overmolded onto the frame 27, the frame 27 being composed of a first material having a first durometer and the body 12 and face seal 26 being composed of a second material having a second durometer, the first durometer being greater than the second durometer. In another aspect of this embodiment, the frame 27 and the body 12 together define at least one opening 24 configured to receive an attachable component.

In another aspect of this embodiment, the face seal 26 further has a transition portion 64 between the standard reflex seal portion 26a and the reverse reflex seal portion 26b. In another aspect of this embodiment, the transition portion 64 is at least substantially planar.

In another aspect of this embodiment, the body 12 further includes at least one attachment element 25 configured to engage a harness.

In another embodiment, a respiratory mask 10 includes a body 12 including an upper portion 20, a lower portion 22, and a face seal 26, the face seal 26 having a convex first seal 26a that extends along a border of the upper portion 20, the convex first seal 26a having a first cross-sectional U shape defining an opening 36 that is directed in a first direction, and a concave second seal 26b extending along a border of the lower portion 22, the concave second seal 26b having a second cross-sectional U shape defining an opening 56 that is directed in a second direction, the first direction and the second direction being at least substantially opposite each other.

In another aspect of this embodiment, the first direction is away from a user's face and the second direction is toward the user's face when the user is wearing the mask 10.

In another aspect of this embodiment, the convex first seal 26a has a first wall 28 extending from the body 12 in the second direction, a second wall 32 extending toward the body 12 in the first direction, the first wall 28 and the second wall 32 being at least substantially parallel, and a sealing land 30 extending between the first wall 28 and the second wall 32.

In another aspect of this embodiment, the concave second seal 26b has a first wall 48 extending from the body 12 in the first direction, a second wall 50 extending from the first wall 48 in a direction different than the first direction and the second direction, and a third wall 52 extending from the second wall 50 in the second direction, the first wall 48 and the third wall 52 being at least substantially parallel. In another aspect of this embodiment, the third wall 52 of the concave second seal 26b includes a sealing surface 55, the third wall 52 being configured to engage in physical contact with the user's face at the sealing surface 55 when the user is wearing the mask 10.

In another aspect of this embodiment, the face seal 26 is integrally formed with a single, unitary construction with the body 12.

In another embodiment, an oronasal respiratory mask includes a frame 27 composed of a first material having a first durometer, and a body 12 composed of a second material having a second durometer that is less than the first durometer, the body 12 being overmolded onto the frame 27 and including a face seal 26, the face seal 26 being integrally formed with a single, unitary construction with the body 12. The face seal 26 has a standard reflex seal portion 26a that has a first wall 28, a second wall 32, a first opening 36 defined between the first wall 28 and the second wall 32, and a first contact surface 30 between the first wall 28 and the second wall 32 oppose the first opening 36, the first wall 28 and the second wall 32 being at least substantially parallel, the first opening 36 being directed in a first direction and the first contact surface being configured to engage in physical contact with a user's face when the user is wearing the mask 10. The face seal further has a reverse reflex seal portion 26b that has a third wall 48, a fourth wall 52, a second opening 56 defined between the third wall 48 and the fourth wall 52, and a second contact surface 55 on the fourth wall 52, the second opening 56 being directed in a second direction, the first direction and the second direction being at least substantially opposite each other, the second contact surface 55 being configured to engage in physical contact with the user's face when the user is wearing the mask 10.

Other embodiments may include:

Embodiment 1

A respiratory mask comprising:
a body configured to cover a nose and a mouth of a user, the body comprising a face seal configured to at least partially seal the body to a face of the user, the face seal comprising a standard reflex seal that is configured to engage in physical contact with the user's face to form a first segment of a seal between the body and the user's face, the face seal further comprising a reverse reflex seal that is configured to engage in physical contact with the user's face to form a second segment of a seal between the body and the user's face.

Embodiment 2

The respiratory mask of Embodiment 1, wherein the standard and reverse reflex seals of the face seal comprises U-shapes having openings that point in different directions from each other.

Embodiment 3

The respiratory mask of Embodiment 1, wherein the standard reflex seal of the face seal comprises a U-shape having an opening that points generally away from the user's face.

Embodiment 4

The respiratory mask of Embodiment 1, wherein the reverse reflex seal of the face seal comprises a U-shape having an opening that points generally toward the user's face.

Embodiment 5

The respiratory mask of Embodiment 1, wherein the standard reflex seal of the face seal comprises a first wall that extends outward from the body to a sealing land at which the standard reflex seal is configured to engage in physical contact with the user's face, the first wall extending outward from the body in a direction that extends generally toward the user's face when the user is wearing the mask, the standard reflex seal comprising a second wall that extends outward from the sealing land in a direction that extends generally away from the user's face when the user is wearing the mask.

Embodiment 6

The respiratory mask of Embodiment 1, wherein the reverse reflex seal of the face seal comprises a first wall that extends from the body to a second wall, the first wall extending outward from the body in a direction that extends generally away the user's face when the user is wearing the mask, the reverse reflex seal comprising a third wall that extends outward from the second wall in a direction that extends generally toward the user's face when the user is wearing the mask, the reverse reflex seal being configured to engage in physical contact with the user's face at a sealing surface of the third wall.

Embodiment 7

The respiratory mask of Embodiment 1, wherein the body comprises a nose area configured to receive the nose of the user therein, the standard reflex seal of the face seal extending along the nose area such that the standard reflex seal is configured to engage in physical contact with the user's face adjacent the user's nose.

Embodiment 8

The respiratory mask of Embodiment 1, wherein the body comprises a mouth area configured to cover the user's mouth, the reverse reflex seal of the face seal extending along the mouth area such that the reverse reflex seal is configured to engage in physical contact with the user's face adjacent the user's mouth.

Embodiment 9

The respiratory mask of Embodiment 1, wherein the standard reflex seal of the face seal is configured to cover upper cheeks and the nose of the user.

Embodiment 10

The respiratory mask of Embodiment 1, wherein the reverse reflex seal of the face seal is configured to cover lower cheeks and a chin of the user.

Embodiment 11

The respiratory mask of Embodiment 1, wherein the face seal is integrally formed with a single, unitary construction with the mask body.

Embodiment 12

The respiratory mask of Embodiment 1, wherein the respiratory mask is a half mask.

Embodiment 13

The respiratory mask of Embodiment 1, further comprising a harness configured to hold the body on the user's face.

Embodiment 14

The respiratory mask of Embodiment 1, wherein the body comprises an opening configured to receive at least one of a filter cartridge, a valve, or an air hose therein.

Embodiment 15

A respiratory mask comprising:
a body configured to cover a nose and a mouth of a user, the body comprising a face seal configured to at least partially seal the body to a face of the user, the face seal comprising a first seal that is configured to engage in physical contact with the user's face to form a first segment of a seal between the body and the user's face, the face seal further comprising a second seal that is configured to engage in physical contact with the user's face to form a second segment of a seal between the body and the user's face, wherein the first and second seals comprise U-shapes having openings that point in different directions from each other.

Embodiment 16

The respiratory mask of Embodiment 15, wherein the opening of the U-shape of the first seal points generally away from the user's face.

Embodiment 17

The respiratory mask of Embodiment 15, wherein the opening of the U-shape of the second seal points generally toward the user's face.

Embodiment 18

The respiratory mask of Embodiment 15, wherein the first seal of the face seal comprises a first wall that extends outward from the body to a sealing land at which the first seal is configured to engage in physical contact with the user's face, the first wall extending outward from the body in a direction that extends generally toward the user's face when the user is wearing the mask, the first seal comprising a second wall that extends outward from the sealing land in a direction that extends generally away from the user's face when the user is wearing the mask.

Embodiment 19

The respiratory mask of Embodiment 15, wherein the second seal of the face seal comprises a first wall that extends from the body to a sealing land at which the second seal is configured to engage in physical contact with the user's face, the first wall extending outward from the body in a direction that extends generally away from the user's face when the user is wearing the mask, the second seal comprising a second wall that extends outward from the sealing land in a direction that extends generally toward the user's face when the user is wearing the mask.

Embodiment 20

The respiratory mask of Embodiment 15, wherein the second seal of the face seal comprises a first wall that extends from the body to a second wall, the first wall extending outward from the body in a direction that extends generally away the user's face when the user is wearing the mask, the second seal comprising a third wall that extends outward from the second wall in a direction that extends generally toward the user's face when the user is wearing the mask, the second seal being configured to engage in physical contact with the user's face at a sealing surface of the third wall.

Embodiment 21

The respiratory mask of Embodiment 15, wherein the face seal is integrally formed with a single, unitary construction with the mask body.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means plus-function format and are not intended to be interpreted based on 35 U.S.C. § 112, sixth paragraph, unless and until such claim limitations expressly use the phrase "means for" followed by a statement of function void of further structure.

It will be appreciated by persons skilled in the art that the invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the invention.

What is claimed is:
1. An oronasal respiratory mask comprising:
a body including an upper portion, a lower portion, and a face seal, the body having an interior side and an exterior side opposite the interior side, the body defining an interior volume, the face seal having:
a standard reflex seal portion in the upper portion; and
a reverse reflex seal portion in the lower portion, the reverse reflex seal portion having a second bottom and a second unobstructed opening, the second bottom and the second unobstructed opening being directly exposed to the exterior side of the body and the standard reflex seal portion being within the interior side of the body.

2. The oronasal respiratory mask of claim 1, wherein:
the standard reflex seal portion has a cross-sectional U shape having a first bottom and a first opening; and
the reverse reflex seal portion has a cross-sectional U shape, the first opening being directed in a first direction and the second opening being directed in a second direction, the first and second directions being different.

3. The oronasal respiratory mask of claim 1, wherein the body further includes an inner surface and an outer surface opposite the inner surface, a direction from the inner surface to the outer surface being a first direction and a direction from the outer surface to the inner surface being a second direction, the standard reflex seal portion having a cross-sectional U shape with an opening that extends in the first direction.

4. The oronasal respiratory mask of claim 3, wherein the standard reflex seal portion includes:
a first wall that extends from the body in the second direction;
a second wall that extends toward the body in the first direction, the first wall and the second wall being at least substantially parallel; and
a contact surface extending between the first wall and the second wall.

5. The oronasal respiratory mask of claim 1, wherein the body further includes an inner surface and an outer surface opposite the inner surface, a direction from the inner surface to the outer surface being a first direction and a direction from the outer surface to the inner surface being a second direction, the reverse reflex seal portion having a cross-sectional U shape with an opening that extends in the second direction.

6. The oronasal respiratory mask of claim 5, wherein the reverse reflex seal portion includes:
a first wall that extends from the body in the first direction;
a second wall that extends from the first wall in a direction different than the first direction and the second direction; and
a third wall that extends from the second wall in the second direction, the first wall and the third wall being at least substantially parallel, the third wall including a contact surface.

7. The oronasal respiratory mask of claim 1, wherein the standard reflex seal portion extends along a border of the upper portion such that the standard reflex seal portion is configured to engage in physical contact with a user's face adjacent the user's nose when the user is wearing the mask.

8. The oronasal respiratory mask of claim 1, wherein the reverse reflex seal portion extends along a border of the lower portion such that the reverse reflex seal portion is configured to engage in physical contact with a user's face adjacent the user's mouth when the user is wearing the mask.

9. The oronasal respiratory mask of claim 1, further comprising a frame, the body being overmolded onto the frame, the frame being composed of a first material having a first durometer and the body and face seal being composed of a second material having a second durometer, the first durometer being greater than the second durometer.

10. The oronasal respiratory mask of claim 9, wherein the frame and the body together define at least one opening configured to receive an attachable component.

11. The oronasal respiratory mask of claim 1, wherein the face seal further has a transition portion between the standard reflex seal portion and the reverse reflex seal portion.

12. The oronasal respiratory mask of claim 11, wherein the transition portion is at least substantially planar.

13. The oronasal respiratory mask of claim 1, wherein the body further includes at least one attachment element configured to engage a harness.

14. An oronasal respiratory mask comprising:
a body including an upper portion, a lower portion, and a face seal, the face seal having:
a convex first seal that extends along a border of the upper portion, the convex first seal having a first cross-sectional U shape defining an opening that is directed in a first direction; and
a concave second seal that extends along a border of the lower portion, the concave second seal having a second cross-sectional U shape defining an opening that is directed in a second direction, the first direction and the second direction being at least substantially opposite each other, the opening of the concave second seal being exposed to an exterior environment of the oronasal respiratory mask.

15. The oronasal respiratory mask of claim 14, wherein the first direction is away from a user's face and the second direction is toward the user's face when the user is wearing the mask.

16. The oronasal respiratory mask of claim 14, wherein the convex first seal has:
a first wall extending from the body in the second direction;
a second wall extending toward the body in the first direction, the first wall and the second wall being at least substantially parallel; and
a sealing land extending between the first wall and the second wall.

17. The oronasal respiratory mask of claim 14, wherein the concave second seal has:
a first wall extending from the body in the first direction;
a second wall extending from the first wall in a direction different than the first direction and the second direction; and
a third wall extending from the second wall in the second direction, the first wall and the third wall being at least substantially parallel.

18. The oronasal respiratory mask of claim 17, wherein the third wall of the concave second seal includes a sealing surface, the third wall being configured to engage in physical contact with the user's face at the sealing surface when the user is wearing the mask.

19. The oronasal respiratory mask of claim 14, wherein the face seal is integrally formed with a single, unitary construction with the body.

20. An oronasal respiratory mask comprising:
a frame composed of a first material having a first durometer;
a body composed of a second material having a second durometer that is less than the first durometer, the body being overmolded onto the frame and including a face seal, the body having an interior side and an exterior side opposite the interior side, the body defining an interior volume, the face seal being integrally formed with a single, unitary construction with the body and having:
a standard reflex seal portion that has a first wall, a second wall, a first opening defined between the first wall and the second wall, and a first contact surface between the first wall and the second wall opposite the first opening, the first wall and the second wall being at least substantially parallel, the first opening being directed in a first direction and the first contact surface being configured to engage in physical contact with a user's face when the user is wearing the mask; and a reverse reflex seal portion that has a third wall, a fourth wall, a second unobstructed opening defined between the third wall and the fourth wall, and a second contact surface on the fourth wall, the second opening being directed in a second direction, the first direction and the second direction being at least substantially opposite each other, the second unobstructed opening being directly exposed to the exterior side of the body, the second contact surface being configured to engage in physical contact with the user's face when the user is wearing the mask, the body being movable relative to the user's face and to the second contact surface without breaking the physical contact between the second contact surface and the user's face.

* * * * *